US008927508B2

(12) United States Patent
Draghia-Akli et al.

(10) Patent No.: US 8,927,508 B2
(45) Date of Patent: Jan. 6, 2015

(54) ANTIBODY PRODUCTION ELICITED BY A DNA VACCINE DELIVERED BY ELECTROPORATION

(75) Inventors: Ruxandra Draghia-Akli, Houston, TX (US); Amir S. Khan, Houston, TX (US)

(73) Assignee: VGX Pharmaceuticals, Inc., Plymouth Meeting, PA (US)

( * ) Notice: Subject to any disclaimer, the term of this patent is extended or adjusted under 35 U.S.C. 154(b) by 315 days.

(21) Appl. No.: 12/271,603

(22) Filed: Nov. 14, 2008

(65) Prior Publication Data

US 2009/0156787 A1 Jun. 18, 2009

Related U.S. Application Data

(60) Provisional application No. 60/988,012, filed on Nov. 14, 2007, provisional application No. 60/988,773, filed on Nov. 16, 2007.

(51) Int. Cl.
| | |
|---|---|
| A61K 48/00 | (2006.01) |
| C12N 13/00 | (2006.01) |
| A61K 39/12 | (2006.01) |
| A61K 39/145 | (2006.01) |
| C12N 15/87 | (2006.01) |
| A61K 39/00 | (2006.01) |

(52) U.S. Cl.
CPC .............. *A61K 39/12* (2013.01); *C12N 13/00* (2013.01); *A61K 39/145* (2013.01); *A61K 48/00* (2013.01); *A61K 2039/53* (2013.01); *A61K 2039/54* (2013.01); *C12N 15/87* (2013.01); *C12N 2760/16134* (2013.01)
USPC .................... 514/44 R; 435/173.1; 435/173.6

(58) Field of Classification Search
None
See application file for complete search history.

(56) References Cited

U.S. PATENT DOCUMENTS

| | | | | | |
|---|---|---|---|---|---|
| 4,297,274 | A | * | 10/1981 | Bohn et al. .................. | 530/389.6 |
| 5,593,972 | A | | 1/1997 | Weiner et al. | |
| 5,883,081 | A | | 3/1999 | Kraus et al. | |
| 5,962,428 | A | | 10/1999 | Carrano et al. | |
| 6,224,870 | B1 | * | 5/2001 | Segal .......................... | 424/192.1 |
| 6,528,315 | B2 | * | 3/2003 | Bureau et al. ............... | 435/461 |
| 6,972,013 | B1 | * | 12/2005 | Zhang et al. ................ | 604/501 |
| 7,238,522 | B2 | | 7/2007 | Hebel et al. | |
| 7,245,963 | B2 | | 7/2007 | Draghia-Akli et al. | |
| 8,209,006 | B2 | | 6/2012 | Smith | |
| 2004/0014645 | A1 | * | 1/2004 | Draghia-Akli et al. ........ | 514/8 |
| 2005/0052630 | A1 | | 3/2005 | Smith et al. | |
| 2008/0091135 | A1 | | 4/2008 | Draghia-Akli et al. | |

FOREIGN PATENT DOCUMENTS

| | | |
|---|---|---|
| JP | WO2007/023725 | 3/2007 |
| WO | 93/24640 A2 | 12/1993 |
| WO | 94/16737 | 8/1994 |

OTHER PUBLICATIONS

Kadowaki et al, Vaccine 2000;18:2779-88.*
Chen et al. Vaccine 2001;19:1446-55.*
Epstein et al. Emerging Infect Dis 2002;8:796-801.*
Pantaleo, G. et al., Immunopathogenesis of HIV Infection, Annu. Rev. Microbiol., 1996;50:825-54.
Soudeyns, H., et al., The moving target: mechanisms of HIV persistence during primary infection, Immunology Today, Oct. 1999;20(10):446-50.
Zhao, J., et al., Improved Protection of Rhesus Macaques against Intrarectal Simian Immunodeficiency Virus SIV mac251 Challenge by a Replication-Competent Ad5hr-SIVenv/rev and Ad5hr-SIVgag Recombinatn Priming/gp120 Boosting Regimen, Journal of Virology, Aug. 2003;77(15):8354-65.
Pal, R., et al., Polyvalent DNA prime and envelope protein boost HIV-1 vaccine elicits humoral and cellular responses and controls plasma viremia in rhesus macaques following rectal challenge with an R5 SHIV isolate, J. Med. Primatol, 2005;35:226-36.
Pal, R., et al., Immunization of rhesus macaques with a polyvalent DNA prime/protein boost human immunodeficiency virus type 1 vaccine elicits protective antibody response against simian human immunodeficiency virus of R5 phenotype, Virology, 2006:348:341-53.
Pal, R., et al., Definitive toxicology and biodistribution study of a polyvalent DNA prime/protein boost human immunodeficiency virus type 1 (HIV-1) vaccine in rabbits. Vaccine, 2006;24:1225-34.
Amara, R. A., et al., Control of a Mucosal Challenge and Prevention of AIDS by a Multiprotein DNA/MVA Vaccine, Science, Apr. 6, 2001,292.69-74.
Barouch, D. H., et al., DNA Vaccination for HIV and SIV, Intervirology, 2000:43:282-87.
Earl, P. L., et al., Immunogenicity and Protective Efficacy of Oligomeric Human Immunodeficiency Virus Type 1 gp140, Journal of Virology, Jan. 2001;75(2)645-53.
Franchini, G., et al., Poxvirus-based vaccine candidates for HIV: two decades of experience with special emphasis on canarypox vectors; Expert Rev. Vaccines, 2004;3(4)-75-88.
Gomez-Roman, V. R., et al., Adenoviruses as Vectors for HIV Vaccines, AIDS Rev, 2003;5:178-85.
Reyes-Sandoval, A., et al., Human Immunodeficiency Virus Type 1-Specific Immune Responses in Primates upon Sequential Immunization with Adenoviral Vaccine Carriers of Human and Simian Serotypes, Journal of Virology, Jul. 2004;78(14):7392-99.

(Continued)

*Primary Examiner* — Janice Li
(74) *Attorney, Agent, or Firm* — Thomas Kim

(57) ABSTRACT

There are provided methods of generating antibodies in a mammal against recombinant antigens using DNA plasmids capable of expressing said antigens in cells of said mammal, comprising: injecting into tissue of said mammal a DNA plasmid comprising an encoding sequence operably linked to a promoter, electroporating said tissue with an electroporation device capable of delivering an electrical pulse effective to electroporate cells of said tissue to allow entry of said DNA plasmid and expression of said antigen, and allowing said mammal to respond to said expressed antigen in order to generate antibodies to said antigen. Furthermore, there are provided methods of isolating antibodies specific against desired antigens wherein said antibodies are generated in a mammal using DNA plasmids capable of expressing said antigens.

41 Claims, 6 Drawing Sheets

(56) References Cited

OTHER PUBLICATIONS

Santra, S., et al., Recombinant poxvirus boosting of DNA-primed rhesus monkeys augments peak but not memory T lymphocyte responses, PNAS, Jul. 27, 2004;101(30):11088-93.

Sumida, S. M., et al., Recruitment and expansion of dendritic cells in vivo potentiate the immunogenicity of plasmid DNA vaccines, The Journal of Clinical Investigation, Nov. 2004;114(9):1334-42.

Mantovani, A., et al., Tumour immunity: effector response to tumour and role of the microenvironment, Lancet., Mar. 1, 2008;371(9614)171-83.

Stephenson, I., et al., Detection of anti-H5 responses in human sera by HI using horse erythrocytes following MF59-adjuvanted influenza A/Duck/Singapore/97 vaccine, Virus Res., Jul. 2004;103(1-2):91-5.

Chastain, M., et al., Antigen levels and antibody titers after DNA vaccination, J Pharm Sci., Apr. 2001;90(4):474-84.

Bodles-Brakhop; A. M., et al., DNA vaccination and gene therapy: optimization and delivery for cancer therapy, Expert Rev Vaccines., Sep. 7, 2008(7):1085-101.

Cristillo, A. D., et al., Preclinical evaluation of cellular immune responses elicited by a polyvalent DNA prime/protein boost HIV-1 vaccine, Virology., Mar. 1, 2006:346(1):151-68.

Beyer, M., et al., Immunoregulatory T cells: role and potential as a target in malignancy, Curr Oncol Rep., Mar. 2008;10(2):130-6.

Curcio, C., et al., DNA immunization using constant-current electroporation affords long-term protection from autochthonous mammary carcinomas in cancer-prone transgenic mice, Cancer Gene Ther., Feb. 2008;15(2):108-14.

Leenaars, M., et al., Critical steps in the production of polyclonal and monoclonal antibodies: evelution and recommendations, Ilar J., 2005;46(3):269-79.

Rovero, S., et al., DNA vaccination against rat her-2/Neu p185 more effectively inhibits carcinogenesis than transplantable carcinomas in transgenic BALB/c mice, J Immunol., Nov. 1, 2000;185(9):5133-42.

Selby, M., et al., Enhancement of DNA vaccine potency by electroporation in vivo, J Biotechnol., Sep. 29, 2000;83 (1-2):147-52.

Draghia-Akli Ruxandra et al: "In vivo electroporation of gene sequences for therapeutic and vaccination applications", Regent Patents on DNA & Gene Sequences vol. 1, No. 3, Nov. 1, 2007, pp. 207-213.

Chen J et al: "Protection against influenza virus infection in BALB/c mice immunized with a single dose of neuraminidase-expressing DNAs by electroporation", Vaccine, Elsevier Ltd, GB, vol. 23, No. 34, Jul. 29, 2005, pp. 4322-4328.

Megede J Z et al: "Evaluation of human immunodeficiency virus type 1 subtype C gag, pol, and gagpol DNA and alphavirus replicon vaccines", Vaccine, Elsevier Ltd, GB, vol. 24, No. 15, Apr. 5, 2006, pp. 2755-2763.

A. Luckay et al: "Effect of Plasmid DNA Vaccine Design and In Vivo Electroporation on the Resulting Vaccine-Specific Immune Responses in Rhesus Macaques" Journal of Virology, vol. 81, No. 10, May 15, 2007, pp. 5257-5269.

Prud'Homme G J et al: "Plasmid-based gene therapy of diabetes mellitus", A Gene Therapy, vol. 14, No. 7, Apr. 2007, pp. 553-564.

Dominick J Laddy et al: "Heterosubtypic protection against pathogenic human and avian influenza viruses via in vivo electroporation of synthetic consensus DNA antigens", PLOS ONE, Public Library of Science, San Francisco, CA; US, vol. 3, No. 6, Jun. 1, 2008, pp. 1-8.

* cited by examiner

Week of Study

Figure 9

Figure 10

ANTIBODY PRODUCTION ELICITED BY A DNA VACCINE DELIVERED BY ELECTROPORATION

CROSS-REFERENCE TO RELATED APPLICATIONS

This application claims the benefit of U.S. Provisional Application No. 60/988,012, filed Nov. 14, 2007 and U.S. Provisional Application No. 60/988,773, filed Nov. 16, 2007, the contents of both of which are incorporated herein by reference.

BACKGROUND

Although naked DNA vaccines delivered by intramuscular or intradermal routes prime both antibody and T-cell responses, the level of the responses are often quite low. The low responses have been thought to be the result of inefficient plasmid delivery, both to the physiological site of interest and the rate of uptake by the cell.

In vivo electroporation techniques are available to assist in the delivery of DNA vaccines to subjects. Often, the DNA vaccination using electroporation techniques utilizes constant voltage electroporators, and such instruments do not consider tissue resistance and thus may give rise to non-optimal plasmid expression, inflammation and possible tissue damage.

In the area of human immunodeficiency virus (HIV) vaccines, the discovery of a prophylactic HIV-1 vaccine capable of eliciting high titered neutralizing antibodies and broad T-cell immunity has been elusive. Given that both arms of the immune system have been found to be integral in the control of HIV-1 disease progression (Pantaleo and Fauci, 1996; Soudeyns and Pantaleo, 1999), their induction remain core requisites of many vaccine research and development efforts. Previous reports have discussed results of studies with mice, rabbits and nonhuman primates showing induction of antibodies and T-cell responses using a polyvalent HIV-1 DNA prime/protein boost vaccine strategy (Cristillo et al., 2006; Pal et al., 2006a; Pal et al., 2005; Pal et al., 2006b). From these studies, as well as findings reported by others (Amara et al., 2001; Barouch and Letvin, 2000; Earl et al., 2001; Franchini et al., 2004; Gomez-Roman and Robert-Guroff, 2003; Reyes-Sandoval et al., 2004; Santra et al., 2004; Sumida et al., 2004; Zhao et al., 2003), DNA immunization delivered via intramuscular or intradermal route of administration, was shown to elicit measureable, but weak antibody and T-cell responses; and, thus, requiring boosting immunizations. Using an adjuvant-formulated recombinant protein, it was shown that both humoral and cellular immune responses that were primed by DNA vaccination could be further augmented (Cristillo et al., 2006; Pal et al., 2006a; Pal et al., 2005; Pal et al., 2006b).

In order to increase immunological priming by DNA immunization, several parameters have been investigated that include DNA dosage and scheduling, co-administration of adjuvant and immunomodulatory agent, and varying immunization strategies and routes of delivery. Such studies have highlighted the utility of electroporation technology in increasing expression of plasmid DNA and augmenting humoral and cellular priming using HIV-1, hepatitis B virus, smallpox, and tuberculosis vaccines. Although several electroporation platforms tested thus far have generated encouraging data, these studies have used constant voltage electroporators to facilitate plasmid delivery, which results in less than immunoprotective outcomes.

Similar issues have been described for cancer therapies. Cancer is a leading cause of death in the world with an estimated 9 million people dying from cancer in 2015, and 11.4 million dying in 2030 [World Health Organization]. Many of these deaths can be avoided with early detection and treatment, while over 40% of cancers are preventable. The overriding need for preventative and therapeutic remedies for the copious forms of cancer is daunting. However, new diagnostic technologies and screening methods as well as new and more effective therapeutic agents are available that altogether are reducing mortality for several cancers [www.cancer.gov]. Furthermore, the recent success of DNA vaccines based on the greater knowledge of tumor immunology in animal models has given hope to the field (e.g. melanoma, prostate cancer).

Although inflammation has been shown to promote oncogenesis (A. Mantovani, P. Romero, A. K. Palucka, F. M. Marincola, Tumour immunity: effector response to tumour and role of the microenvironment Lancet 371, (2008) 771-783), the immune system may also be utilized in the fight against cancer. The field of tumor immunology has evolved since the identification of the first tumor antigen in a human melanoma cell line in 1991, namely "MAGE" (melanoma Ag), that elicited a cytotoxic T-lymphocyte (CTL) response. Furthermore, it was discovered that this antigen is encoded by a normal, non-mutated gene that is activated in many melanomas and in some other cancers but remains silent in normal tissues. The presence of antigens on the surface of tumor cells recognized by cytotoxic and T helper lymphocytes is essential for effective immune responses and for the development of specific cancer vaccines. Unfortunately, the development of cancer vaccines for established cancers has not proven effective. The use of antibodies to tumor antigens has had limited success in treating specific types of cancer, possibly due to the action of regulatory T-cells. Regulatory T-cells normally function to restrain the activity of the immune response and have been associated with prevention of antitumor immunity (M. Beyer, J. L. Schultze, Immunoregulatory T cells: role and potential as a target in malignancy Curr. Oncol. Rep. 10, (2008) 130-136). Mechanisms of tolerance and immunoescape have also limited the clinical outcome of cancer vaccination, including DNA vaccines. In order to overcome these drawbacks and augment the immune response several lines of action are required. Firstly, it is important to identify the tumor antigens that are to be targeted. Secondly, the desired immune response needs to be defined and the optimal vaccine engineered. Finally, efficient delivery of the vaccine is essential for success (Bodles-Brakhop A M, Draghia-Akli R. DNA vaccination and gene therapy: optimization and delivery for cancer therapy. Expert Rev Vaccines. 2008 September; 7(7):1085-101).

Curcio et. al. Cancer Gene Therapy (2007) entitled "DNA immunization using constant-current electroporation affords long-term protection from autochthonous mammary carcinomas in cancer-prone transgenic mice," which is noted as being published on-line in early November, 2007, discusses the use of electroporation facilitated DNA delivery methods and generating antibodies in mice against ErbB-2, Her-2/neu.

There still remains a need for a delivery method for DNA plasmids that yields antigen expression levels that can elicit a strong immune response and also generate neutralizing antibodies.

SUMMARY OF THE INVENTION

An aspect of the present invention includes methods of generating antibodies in a mammal against recombinant antigens using DNA plasmids capable of expressing said antigens in cells of said mammal. These methods include the steps of injecting into tissue of said mammal a DNA plasmid comprising an encoding sequence operably linked to a promoter; electroporating said tissue with an electroporation device capable of delivering an electrical pulse effective to electroporate cells of said tissue to allow entry of said DNA plasmid and expression of said antigen; and allowing said mammal to respond to said expressed antigen in order to generate antibodies to said antigen.

In another aspect, there are methods of isolating antibodies specific against desired antigens wherein said antibodies are generated in a mammal using DNA plasmids capable of expressing said antigens in cells of said mammal. These methods includes the steps of injecting into tissue of said mammal a DNA plasmid comprising an encoding sequence operably linked to a promoter; electroporating said tissue with an electroporation device capable of delivering an electrical pulse effective to electroporate cells of said tissue to allow entry of said DNA plasmid and expression of said antigen; allowing said mammal to respond to said expressed antigen in order to generate antibodies to said antigen; collecting serum from said mammal; and extracting said antibodies from the serum. In some embodiments, there is a further step of purifying the extracted antibodies.

BRIEF DESCRIPTION OF THE DRAWINGS

The numerous objects and advantages of the present invention may be better understood by those skilled in the art by reference to the accompanying figures, in which:

FIG. 9 displays a bar graph of results from HI titers in ferrets after vaccination; the assay was performed using reassortant viruses obtained from the Center for Disease Control: A/Viet/1203/04 or Indo/05/2005 influenza strains.

FIG. 10 displays a bar graph of results from HI titers measured three weeks after the second immunization. Macaques immunized ID followed by EP showed significantly higher HI titers than all other groups (P<0.03). Non-treated controls did not exhibit any HI titers.

DETAILED DESCRIPTION OF PREFERRED EMBODIMENTS

Figure 1:
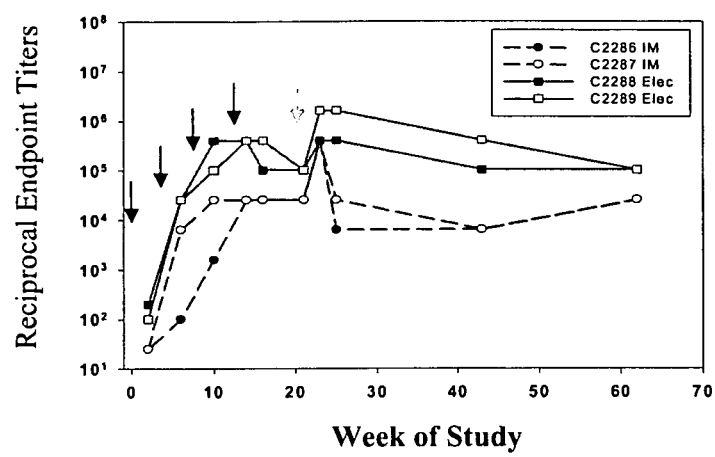
FIG. 1 displays a graph representing ELISA assays performed using rabbit and macaque sera. Rabbits (top panel) and macaques (bottom panel) were immunized with plasmid DNA at the time points indicated (black arrows) followed by intramuscular protein boost (grey arrow). Antibody titers are based on the dilution of immune serum producing two times the optical density at 450 nm compared with the corresponding dilution of pre-immune serum.
Figure 1:
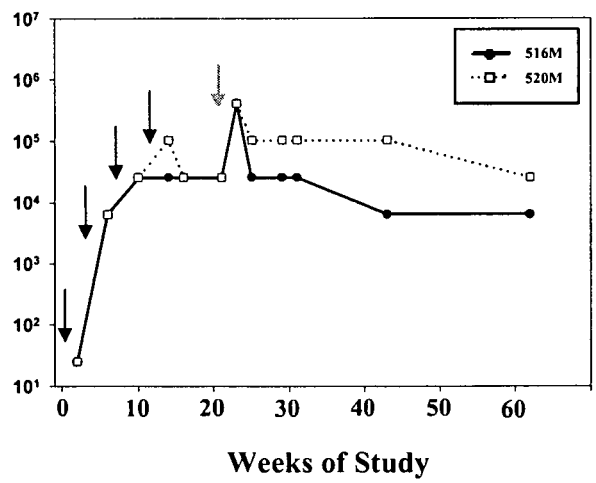

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided EP devices, which comprises measuring the current in tissue between electrodes and altering the energy output delivered by the EP device accordingly in order to maintain the current at a constant level throughout the target tissue. This constant level is preset by a user prior to initiation of a pulse sequence or electrical treatment. Preferably, the feedback is accomplished by the electroporation component, e.g., controller, of the EP device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP") as used interchangeably herein refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

An aspect of the present invention includes methods of generating antibodies in a mammal against recombinant antigens using DNA plasmids capable of expressing said antigens in cells of said mammal. These methods include the steps of injecting into tissue of said mammal a DNA plasmid comprising an encoding sequence operably linked to a promoter; electroporating said tissue with an electroporation device capable of delivering an electrical pulse effective to electroporate cells of said tissue to allow entry of said DNA plasmid and expression of said antigen; and allowing said mammal to respond to said expressed antigen in order to generate antibodies to said antigen.

In another aspect, there are methods of isolating antibodies specific against desired antigens wherein said antibodies are generated in a mammal using DNA plasmids capable of expressing said antigens in cells of said mammal. These methods includes the steps of injecting into tissue of said mammal a DNA plasmid comprising an encoding sequence operably linked to a promoter; electroporating said tissue with an electroporation device capable of delivering an electrical pulse effective to electroporate cells of said tissue to allow entry of said DNA plasmid and expression of said antigen; allowing said mammal to respond to said expressed antigen in order to generate antibodies to said antigen; collecting serum from said mammal; and extracting said antibodies from the serum. In some embodiments, there is a further step of purifying the extracted antibodies.

In some embodiments, there is a further step of repeating the injecting DNA plasmid step, the electroporating tissue step, and the allowing said mammal to respond step in the same mammal at a subsequent day. Furthermore, in some examples, this repeating step can be further repeated on another subsequent day. In some embodiments, there is an additional step of delivering a protein boost of the antigen (in other words, the protein version) to the same mammal on a subsequent day (or subsequent day from the prior DNA plasmid injection).

In some embodiments the injecting step includes injecting into intradermic or intramuscular tissue of the mammal.

The antibodies provided herein are antibodies produced by the humoral immune system of the mammals injected with the DNA plasmids. The antibodies are specific for the recombinant antigens that are expressed from the DNA plasmids. The antibodies can be one of the many existing isotypes, but are preferably of the IgG1 and IgG2 isotypes, and more preferably IgG2a isotype.

The antibodies produced by the mammals using the methods provided herein are extracted and purified using known techniques available to a skilled artisan, including those described in Leenaars, M. and Hendriksen, C. F. M., *Inst. Lab. Animal Res.* 46(3) (2005). The steps to isolate antibodies generated by the treated mammals includes steps of collecting serum from the mammal and extracting the antibodies from the collected serum. In some instances, the steps can further include a step of purifying the extracted antibodies.

In some embodiments, the recombinant antigens are antigenic portions of proteins identified as immunogenic, the proteins being protein components of cancer markers, e.g., neu oncogene, or viruses, e.g., hemagglutinin (HA) for influenza virus. The recombinant antigens are preferably in the form of encoding sequences that are cloned into a DNA vector such as for example pVAX for eventual transfection of mammalian cells and expression therefrom, although other vehicles for delivering same encoding sequences are not excluded. In some embodiments the recombinant antigens are immunogenic antigens selected from the following, although not an exhaustive list: breast cancer, such as ErbB or Her2/neu; prostate cancer, such as PSA or PSMA; dengue virus, such as DIII domain antigen from one or more subtypes; influenza virus, such as HA, neuraminidase (NA), nucleoprotein (NP), matrix protein, chimera M2e-NP; HIV virus, such as env, gag, pol; west nile virus, such as portions of the capsid protein; and other cancer markers or viral proteins.

In some embodiments, the electroporation is performed by an electroporation device that is capable of delivering an electrical pulse to electroporate cells of a mammal to which the DNA plasmid was delivered. The electroporation devices that are preferred are discussed herein and are further included by incorporation by reference. Preferably, the electroporation devices are constant-current electroporation devices, which preferably provides a constant current throughout the pulse duration. The preferred electroporation devices are capable of delivering an electrical pulse of the following current ranges: about 0.01 Amp to about 10.0 Amp; about 0.01 Amp to about 5.0 Amp; about 0.01 Amp to about 3.0 Amp; about 0.01 Amp to about 1.0 Amp; about 0.05 Amp to about 10.0 Amp; about 0.05 Amp to about 5.0 Amp; about 0.05 Amp to about 3.0 Amp; about 0.05 Amp to about 1.0 Amp; about 0.1 Amp to about 10.0 Amp; about 0.1 Amp to about 5.0 Amp; about 0.1 Amp to about 3.0 Amp; about 0.1 Amp to about 1.0 Amp; about 1.0 Amp to about 10.0 Amp; about 1.0 Amp to about 8.0 Amp; about 1.0 Amp to about 5.0 Amp; about 1.0 Amp to about 4.0 Amp; about 1.0 Amp to about 3.0 Amp; about 1.0 Amp to about 2.0 Amp; about 1.0 Amp; or about 2.0 Amp.

In some embodiments, the pulse pattern of the electrical pulse delivered by the electroporation devices are particularly selected, and can include the following parameters: number of pulses, time between pulses, and pulse length. The number of pulses can be greater than one, and preferably 2 or 3 pulses, and more preferably 3 pulses. In some embodiments, there is a lag time between of pulses during the delivery of an electrical pulse, and preferably the lag time is about 10 sec, about 9 sec, about 8 sec, about 7 sec, about 6 sec, about 5 sec, about 4 sec, about 3 sec, about 2 sec, about 1 sec, about 0.8 sec, about 0.5 sec, or about 0.2 sec, and more preferably the lag time is about 1 sec. The duration of each pulse can vary from about 0.1 msec to about 10 sec, and is preferably from about 1 msec to about 100 msec, about 1 msec to about 80 msec, about 1 msec to about 60 msec, about 1 msec to about 40 msec, about 1 msec to about 20 msec, and more preferably is about 52 msec.

The DNA plasmid is one that includes an encoding sequence of a recombinant antigen that is capable of being expressed in a mammalian cell, upon said DNA plasmid entering after electroporation. Preferably, the encoding sequence is a consensus antigen that elicits an immune response in the target mammal. In some embodiments, the encoding sequence is constructs were optimized for mammalian expression, which can include one or more of the following: including the addition of a Kozak sequence, codon optimization, and RNA optimization. In some embodiments, these optimized encoding sequences can be subcloned into the pVAX vector (Invitrogen, Carlsbad, Calif.).

In some embodiments, the DNA plasmid can be manufactured, preferably in large scale quantities, using a process that is enhanced for high yield and/or cGMP manufacturing. Preferably, the DNA plasmid that is manufactured for delivery to mammals can be formulated into high DNA concentrations. The DNA plasmid manufacturing process can be performed by transfecting microbial cells, such as *E. coli* cells. The processes contemplated for manufacturing DNA plasmids described herein include that disclosed in U.S. Pat. No. 7,238,522 and improved processes in a U.S. patent application having Ser. No. 12/126,611 (filed May 23, 2008, which has yet to publish), which both are hereby incorporated in their entirety. The DNA plasmids are preferably formulated to be safe and effective for injection into mammal subjects. Preferably, the DNA plasmids are formulated to be in concentrations Electroporation and Electroporation Devices Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

Vaccines and Formulations

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Pat. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1☐, MIP-1☐, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The pharmaceutical compositions according to the present invention comprise DNA quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus influenza antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus influenza antigen, described above. The one or more of CTACK protein, TECK protein, MEC protein and functional fragments thereof may be administered prior to, simultaneously with or after administration of the DNA plasmid influenza vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with the EP devices described herein have high DNA concentrations, preferably concentrations that include gram quantities of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in a commonly owned, co-pending U.S. provisional application U.S. Serial No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a commonly owned patent, U.S. Pat. No. 7,238,522, which issued on Jul. 3, 2007. The high concentrations of plasmids used with the EP devices and delivery techniques described herein allow for administration of plasmids into the intradermic/subcutaneous space or, when necessary (due to dose) intramuscularly, in a reasonably low volume and aids in enhancing expression and immunization effects. The commonly owned application and patent, U.S. Ser. No. 60/939,792 and U.S. Pat. No. 7,238,522, respectively, are hereby incorporated in their entirety.

Example 1

Antibodies to HIV-1 env

Materials and Methods
Antigens and Peptides

CMV promoter-driven plasmids encoding codon optimized HIV-1 env (Ba-L) and p55 gag (96ZM651) genes were prepared as provided in Cristillo, A. D., et al., *Virology* 346 (1), 151-68 (2006). Recombinant gp120 (clade B) was expressed in stably transfected CHO cells, under control of the CMV promoter, and purified as reported previously in Cristillo, et al. (2006). Recombinant HIV-1 HXB2 p41 protein was expressed and purified from transformed BL21 (DE3) *Escherichia coli*. Proteins were formulated with QS-21 adjuvant (Antigenics Inc., Woburn, Mass.). HIV-1 Env (BaL) and Gag (HXB2) peptides were synthesized (Infinity Biotech Research and Resource Inc, Aston, Pa.).

Anti-Envelope Binding and Neutralizing Antibodies Induced by Electroporated DNA

New Zealand White rabbits were immunized as outlined in the Materials and Methods section, above. Anti-gp120 antibodies were detected following a single administration of DNA by electroporation that was not observed when DNA was delivered by IM route (FIG. 1, top panel). Titers were found to increase following three additional DNA administrations (FIG. 1, top panel, black arrow) by either route, and were found to be significantly greater (p<0.0001) in rabbits immunized by electroporation as compared to those immunized by IM route at 2 weeks post final DNA immunization (week 14). This finding is of particular interest given that five fold less DNA was used for immunization by electroporation (200 μg) as compared to IM (1 mg) delivery. A single administration of QS-21 formulated gp120 protein by IM route (FIG. 1, top panel, gray arrow) yielded antibody titers that were comparable in both DNA-primed groups. When rabbits were rested, antibody levels in the group primed with IM-delivered DNA were found to decline with rapid kinetics than those in the electroporation group. This was evident from the titers observed on week 62 (41 weeks post final immunization) between electroporation and IM groups (p<0.0001).

Since macaques were electroporated with plasmids encoding both env and gag genes, it was of interest to assess whether induction of antibodies to both antigens would be induced following immunization. In macaques, measurable anti-gp120 antibodies were detected following two DNA immunizations, which antibodies were increased following a third immunization (FIG. 1, bottom panel). Consistent with our findings in rabbits, a fourth DNA administration did not further augment antibody titers markedly.

DNA-primed macaques were then rested for 9 weeks before boosting with QS21-formulated protein. Further increase of anti-Env antibody titers was observed following boosting of macaques with gp120 protein. This antibody level persisted over the course of the next 41 weeks as demonstrated from the titers measured on week 62. Similar induction of anti-Gag antibodies was also noted in these animals following DNA electroporation, although these levels were found to decay at a faster rate than anti-gp120 antibodies (data not shown). Moreover, boosting of DNA-primed animals with recombinant gp41 Gag protein augmented antibody responses, however, the levels were also lower than the anti-Env antibody titers following protein boost (data not shown).

Figure 2:
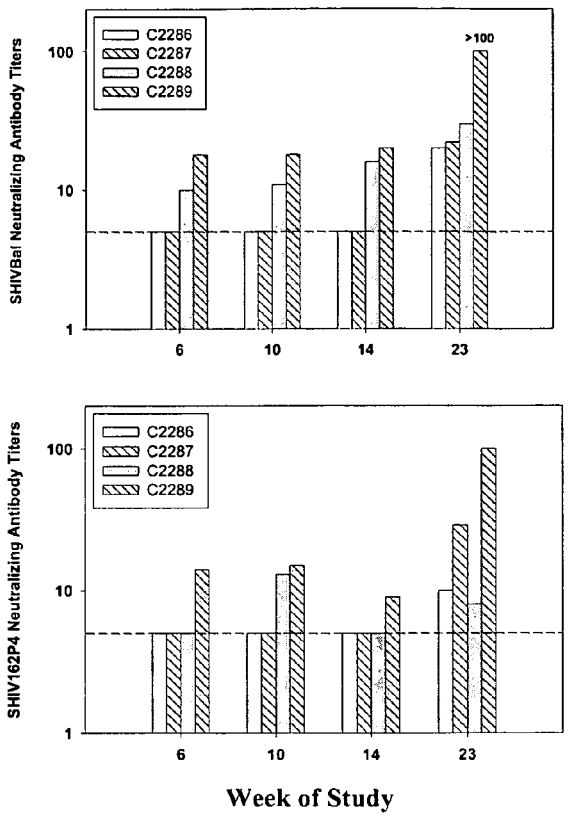
FIG. 2 displays a graph representing neutralization (A, B) assays performed using rabbit and macaque sera. Antibody titers are based on the dilution of immune serum producing two times the optical density at 450 nm compared with the corresponding dilution of pre-immune serum. Neutralization assays were conducted against SHIVBa-L (A, B; top panels) and SHIV162P4 (A, B, bottom panels) isolates using TZMb1 cells. Titers are shown as dilution of immune serum showing 50 percent inhibition of infection compared to untreated controls. The lowest serum dilution tested in the assay was 1.5 as indicated (dotted line). For macaques (B) sera were assayed prior to immunization (pre) and on weeks 6 and 23 of the study.
Figure 2:
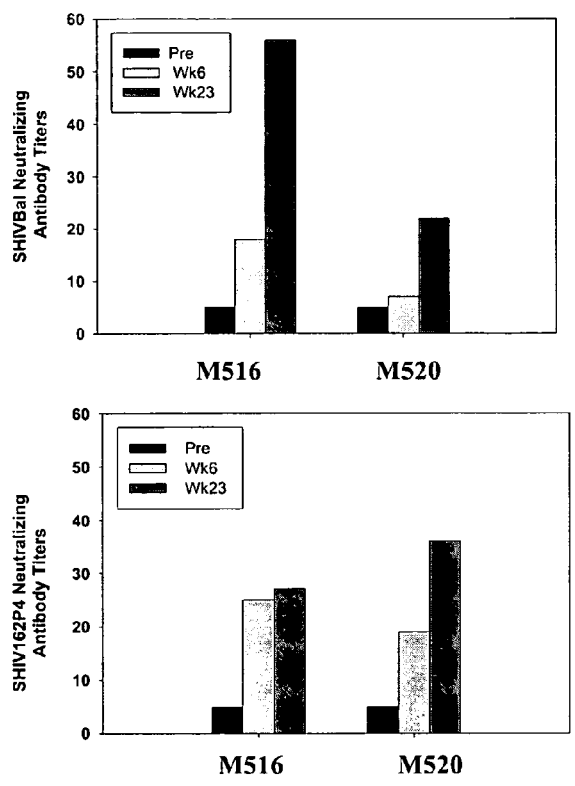

Functional properties of the immune sera were evaluated by assaying neutralization of homologous ($SHIV_{Ba-L}$) and heterologous ($SHIV_{162P4}$) isolates. Neutralizing antibodies to $SHIV_{Ba-L}$ (FIG. 2A upper panel) and $SHIV_{162P4}$ (FIG. 2A, lower panel) were not detected in rabbit serum by week 14 following four DNA immunizations by IM route. However, such antibodies were clearly detected in both neutralization-sensitive isolates in the sera of rabbits immunized by electroporation following two DNA administrations. When DNA-primed rabbits were boosted with a single IM administration of gp120/QS-21, neutralizing antibody titers were found to increase in both DNA-primed groups, yet the levels were higher in rabbits where DNA was delivered by electroporation as compared to IM route.

Similar neutralizing antibodies to $SHIV_{Ba-L}$ (FIG. 2B, upper panel) and $SHIV_{162P4}$ (FIG. 2B, lower panel) were detected in the serum of macaques following two DNA electroporations (week 6). In addition, these titers were further boosted at week 23, two weeks following an IM protein boost.

Antibody levels in nonhuman primates (FIG. 1, bottom panel) were found to persist for up to 62 weeks of the study. Similarly, the kinetics of antibody decline in rabbits (FIG. 1, top panel) was observed to be more rapid in animals immunized by IM route as compared to those immunized by electroporation.

Example 2

Antibodies to p185$^{neu}$

Female BALB/c mice (6-weeks old) were purchased at Charles River Laboratories (Calco, Italy). BALBneuT$^{664V-E}$ mice were bred under specific pathogen-free conditions by Charles River (Calco, Italy). BALBneuT$^{664V-E}$ mice knocked out for Fc-γRI/III (BALBneuT$^{664V-E}$/FcγRI/III) were generated by crossing BALBneuT$^{664V-E}$ mice with BALB/c mice KO for the FcγRI/III receptor, kindly provided by Dr R Clynes (Columbia University, NY). Mammary glands were inspected at weekly intervals to note tumor appearance. Tumor masses were measured with calipers in two perpendicular diameters. Progressively growing masses of more that 1 mm mean diameter were regarded as tumors. Percentage of mice without tumor (tumor-free mice) was evaluated. Mice were treated according to the European Union guidelines.

Plasmid and Electroporation

The pcDNA3 vector coding the extracellular and transmembrane domains of p185$^{neu}$ (EC-TM plasmid) was produced and used as previously described (Rovero S, et al., *J Immunol* 2000; 165:5133-5142). DNA was precipitated, suspended in sterile saline at 1 mg/ml, and stored in aliquots at −20° C. for use in immunization protocols.

For DNA electroporation, EC-TM or pcDNA3 plasmid in 25 µl sterile water with 0.1% poly-L-glutamate were injected into the gastrocnemius muscle of anesthetized mice. Animals were injected with 5-50 µg of plasmid at each time specified. Two constant-current square-wave pulses of 20 ms in duration of 1 s between pulses were applied after 4 s using CEL-LECTRA® adaptive electroporation device and skin electrode assembly (VGX Pharmaceuticals, The Woodlands, TX.). Electrodes of the skin electrode assembly are in an isosceles triangle shape with the long sides 5 mm and the short side 3 mm apart. A constant-current setting of 0.2 A was used for all cancer vaccine experiments, except for the electroporation conditions experiment in which 0.2 A, 0.3 A and 0.4 A were used. The muscle resistance was measured to be between 800 and 1000Ω, with the calculated voltage between 160 V and 195 V.

Assessment of Anti-p185$^{neu}$ Antibody

Sera from BALB/c mice were collected 2, 4 or 6 weeks after vaccination and diluted 1:50 in PBS-azide-bovine serum albumin (PBS-azide-BSA) (Sigma-Aldrich, St. Louis, Mo.). The presence of anti-p185$^{neu}$ antibodies was determined by flow cytometry using BALB/c NIH3T3 fibroblasts, wild-type or stably co-transfected with the wild-type p185$^{neu}$ mouse class I H-2 $K^d$ and B7.1 genes (BALB/c NIH3T3-NKB). FITC-conjugated goat anti-mouse antibodies specific for mouse IgG Fc (Dako-Cytomation, Italy), were used to detect bound primary antibodies. Normal mouse serum was the negative control. The monoclonal Ab4 antibodies (Oncogene Research Products, Cambridge, Mass., USA), which recognizes an extracellular domain of p185$^{neu}$ protein, were used as a positive control. Serial Ab4 dilutions were used to generate a standard curve to determine the concentration (mg/ml) of anti-p185$^{neu}$ antibodies in serum. Flow cytometry analysis was performed with CyAn ADP (DakoCytomation, Italy). Isotype determination was carried out by an indirect immunofluorescence procedure.

Sera was diluted 1:20 in PBS-azide-BSA and were incubated with 2×10$^5$ BALB/c NIH3T3-NKB cells for 45 min at 4° C. After washing, the cells were incubated for 30 min with rat biotin-conjugated antibodies antimouse IgG1, IgG2a, IgG2b and IgG3 (Caltag Laboratories, Burlingame, Calif.), and then for 30 min with 5 ml of streptavidin-phycoertrin (DAKO) and resuspended in PBS-azide-BSA containing 1 mg/ml propidium iodide. Samples were evaluated by CyAn ADP and data are reported as the percentage of p185$^{neu}$+cells.

Induction of Anti-p185neu Response in Wild-type BALB/c Mice

Figure 3:
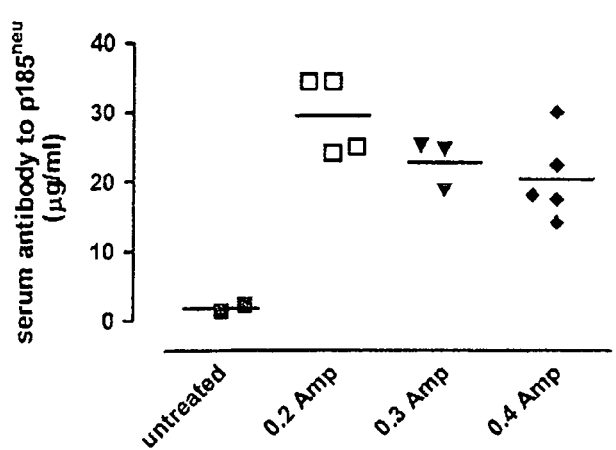
FIG. 3 displays a graph representing optimal current voltage for EC-TM plasmid electroporation assessed in function of the serum antibody. BALB/c mice were vaccinated with 50 mg of EC-TM plasmid and electroporated with 0.2, 0.3 or 0.4 A. Two weeks later sera were collected and the specific antibody titers were evaluated. The graph shows a trend toward an inverse correlation between the current intensity (Amperes) of CCE and the antibody response. Each symbol indicates the average sera of an individual mouse, while the horizontal bars indicate the median value.
Figure 4:
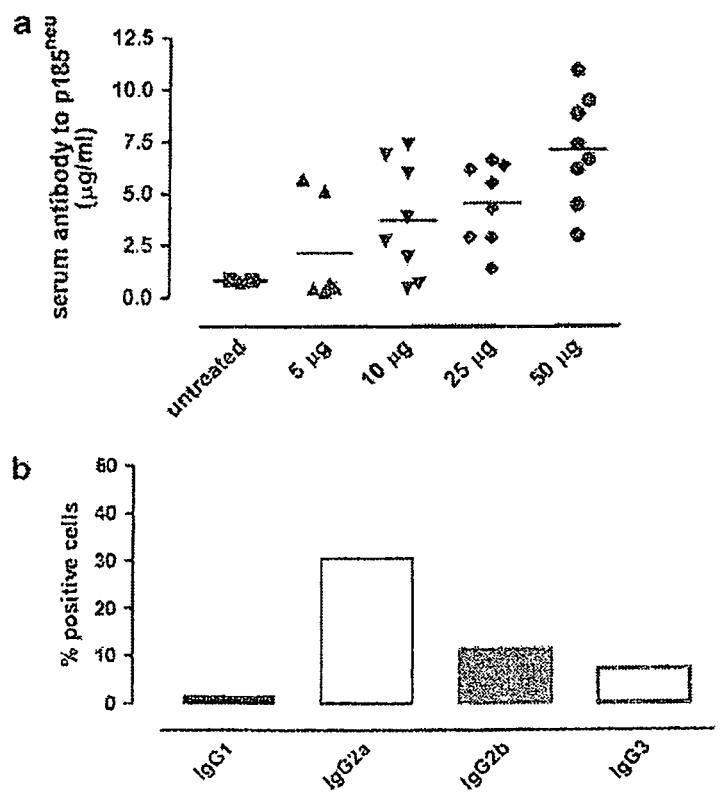
FIG. 4a displays a graph representing induction of $p185^{neu}$ antibody response in BALB/c mice. The mice were vaccinated with 5, 10, 25 and 50 μg of EC-TM plasmid and 0.2 A CCE. Anti-$p185^{neu}$ antibody titers in sera collected 4 weeks after vaccination. The mean titer of antibody appears to increase with the amount of plasmid injected. The antibody titer of mice vaccinated with 50 μg plasmid was significantly higher from those vaccinated with 5, 10 and 25 μg (P=0.0041, 0.0244 and 0.0424 respectively). Each symbol depicts the average sera of an individual mouse, while the horizontal bars indicate the median value.
FIG. 4b displays a bar graph representing induction of $p185^{neu}$ antibody response in specific isotypes. Sera from individual mice were collected 2 weeks after electroporation and pooled to evaluate isotype composition of anti-$p185^{neu}$ antibodies. Data are reported as the percentage of $p185^{neu+}$ cells stained after incubation with immune sera and specific anti-IgG subclasses FITC-conjugated antibodies.

Mice were injected with 50 µg of EC-TM plasmid and administered constant current electroporation (CCE) at different constant current-settings from 0.2 A-0.4 A (FIG. 3). Since, the most evident immune response induced by vaccination with EC-TM plasmids is the rise of anti-p185$^{neu}$ antibodies, two weeks after vaccination sera were collected and the specific antibody titers were evaluated. The titer of anti-p185$^{neu}$ antibodies elicited appears to be inversely proportional to the intensity of the electric current amperage. The lowest current setting, 0.2 A, was used for all the other experiments. Induction of antibodies to p185$^{neu}$ protein was evaluated in mice constant current electroporated with increasing doses of EC-TM plasmid. Sera from individual mice collected 2 and 4 weeks after CCE showed that all doses of EC-TM plasmid were able to induce anti-p185$^{neu}$ antibodies at both 2 (data not shown) and 4 weeks after vaccination. Four weeks after electroporation, sera from mice constant current electroporated with 50 µg of EC-TM plasmid showed the highest titers (FIG. 4a). In addition, sera collected 2 weeks after CCE were pooled to evaluate isotype composition of anti-p185$^{neu}$ antibodies, showing that the 0.2 A condition strongly induces an isotype switch to IgG2a (FIG. 4b), the most effective one for antitumor activity against neu+tumors.

Constant current electroporation with the current setting (0.2 A) in cancer vaccine experiments induces effective levels of IgG2 antibodies. Higher current settings (0.3 and 0.4 A) yielded less efficient electroporations, possibly with more muscle damage, leading to a decrease in EC-TM plasmid expression and thus, specific antibody titers.

Example 3

Antibodies to SEAP in Mice

Plasmid Constructs

Figure 5:
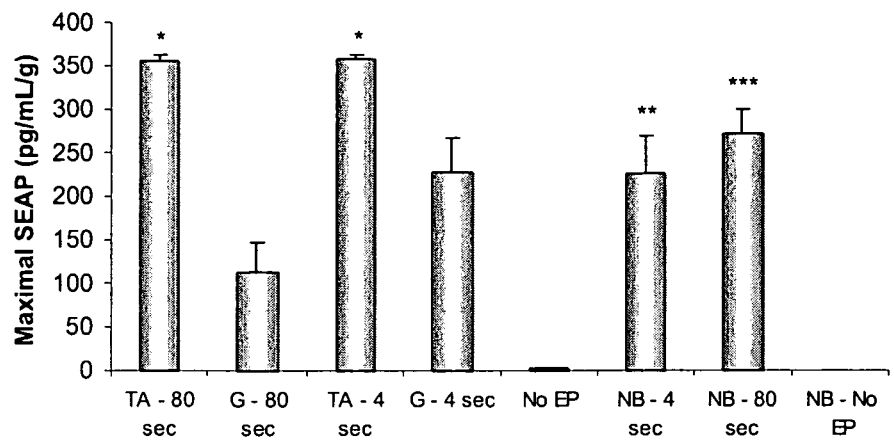
FIG. 5 displays SEAP expression levels measured in different muscles in mice. Animals were injected with 10 μg C5-12-SEAP plasmid in the tibialis anterior (TA) muscle or gastrocnemius (G) muscle and EP after either 4 s or 80 s delay. Animals were also injected with 10 μg pf C5-12-SEAP plasmid without EP (no EP). Serum SEAP levels were higher in TA muscle and G muscle injected animals compared to control animals that received the plasmid without EP (*P<1.3 E-21). Animals injected with the expression cassette without the plasmid backbone (NB) and then electroporated had higher SEAP levels than NB group without EP. However, the NB groups were significantly lower than animals administered C5-12-SEAP in the identical muscle (NB 4 s compared to TA 4 s P<0.008; NB 80 s compared to TA 80 s *P<0.004). Animals injected into the TA muscle yield higher expression than animals injected into the G muscle and lowering the delay between injection and EP in the TA muscle from 80 s to 4 s did not affect expression.

A ubiquitous cytomegalovirus (CMV) promoter drives the expression of human secreted embryonic alkaline phosphatase (SEAP) reporter transgene product in the pCMV-SEAP vector. Plasmids were obtained using a commercially available kit (Qiagen Inc., Chatsworth, Calif.). Endotoxin levels were at less than 0.01 EU/µg, as measured by Kinetic Chromagenic LAL (Endosafe, Charleston, S.C.). Consensus HA and NA constructs were generated by analyzing primary virus sequences from 16H5 viruses that have proven fatal to humans in recent years, and over 40 human N1 viruses. These sequences were downloaded from the Los Alamos National Laboratory's Influenza Sequence Database. After generating the consensus sequences, the constructs were optimized for mammalian expression, including the addition of a Kozak sequence, codon optimization, and RNA optimization. These constructs were then subcloned into the pVAX vector (Invitrogen, Carlsbad, Calif.). Unless indicated otherwise, plasmid preparations were diluted in sterile water and formulated 1% weight/weight with poly-L-glutamate sodium salt (LGS) (MW=10.5 kDa average)(Sigma, St. Louis, Mo.), further HPLC purified at VGX Pharmaceuticals, Immune Therapeutics Division (The Woodlands, Tex).

Injection of Expression Constructs into Mice

In a first experiment, groups of C57/B16 mice (n=10/group) were injected with 10 μg of a plasmid expressing SEAP under the control of a muscle-specific synthetic promoter (pSPc5-12-SEAP) into the tibialis anterior (TA) or gastrocnemius (G) muscle at a lag time of 4 or 80 seconds and 0.1 A constant current. A control group received the plasmid in the TA without EP (No EP). Additional groups of animals received in equal molar concentration an expression cassette with no plasmid backbone (NB), but identical promoter, transgene and 3' polyadenylation signal, in TA and G muscles with and without EP.

In a second mouse experiment, 16 groups×5 mice per group for a total of 80 mice were used (TABLE 1). Mice (n=5/group) were injected with 50 μg of CMV-SEAP (at 10 mg/mL) at varying formulations (saline, saline+1% LGS, water, water+1% LGS) and current intensities. Animals were electroporated with 4 seconds lag time with varying current (0.1 A to 0.2 A) for IM injection in the TA or G muscle.

In all cases, animals were acclimated for 3 days, weighed and ear-tagged. Food and water were available ad libitum for the length of the experiment. On Study Day 0 animals were weighed, bled and anesthetized using the combination anesthetic for rodents—xylazine (37.5 mg/mL; 0.05 mL/30 grams body weight), ketamine (1.9 mg/mL; 0.016 mL/10 grams body weight), acepromazine (0.37 mg/mL; 0.025 mL/15 grams body weight), plasmid was administered per design and electroporated.

On days 0, 4, 7, and 11, mice were weighed and blood collected via retro-orbital bleed into microfuge tubes, respectively. Blood was allowed to clot for 10 to 15 min at room temperature and subsequently centrifuged at 3000×g for 10 min and the serum stored at −80° C. until further analysis.

TABLE 1

Groups for the CMV-SEAP formulation experiment in mice

| Group | Formulation | Conc (mg/mL) | Total Dose (μg/animal) | EP | n |
|---|---|---|---|---|---|
| 1 | Saline | 10 | 50 | 0.2 | 5 |
| 2 | Saline | 10 | 50 | 0.1 | 5 |
| 3 | Saline | 10 | 50 | 0.2 | 5 |
| 4 | Saline | 10 | 50 | 0.1 | 5 |
| 5 | Saline + LGS | 10 | 50 | 0.2 | 5 |
| 6 | Saline + LGS | 10 | 50 | 0.1 | 5 |
| 7 | Saline + LGS | 10 | 50 | 0.2 | 5 |
| 8 | Saline + LGS | 10 | 50 | 0.1 | 5 |
| 9 | Water | 10 | 50 | 0.2 | 5 |
| 10 | Water | 10 | 50 | 0.1 | 5 |
| 11 | Water | 10 | 50 | 0.2 | 5 |
| 12 | Water | 10 | 50 | 0.1 | 5 |
| 13 | Water + LGS | 10 | 50 | 0.2 | 5 |
| 14 | Water + LGS | 10 | 50 | 0.1 | 5 |
| 15 | Water + LGS | 10 | 50 | 0.2 | 5 |
| 16 | Water + LGS | 10 | 50 | 0.1 | 5 |

SEAP Assay

Serum samples were thawed and 50 μL was assayed for SEAP activity using the Phospha-Light Chemiluminescent Reporter Assay Kit (Applied Biosystems, Bedford, Mass.). The lower limit of detection for the assay is 3 pg/mL. More concentrated serum samples were diluted 1:10 in control species-specific serum before assaying for SEAP activity. All samples were read using LUMIstar Galaxy luminometer (BMG Labtechnologies, Offenburg, Germany).

SEAP Indirect ELISA

Immunogenicity to the human SEAP protein was measured in mice using modified procedure from Chastain et al. *J Pharm Sci* 2001 April; 90(4):474-84. Nunc Maxisorb (Rochester, N.Y.) plates were coated with purified human placental alkaline phosphatase in PBS (100 μl containing 100 nanograms/well of human placental alkaline phosphatase (Sigma)) overnight at 4° C. Plates were decanted and washed three times. Plates blocked using 1% BSA (Sigma) in 0.05% Tween 20 in PBS (blocking solution) and incubated for 2 hours room temperature. Serum samples were diluted 1:100 followed by serial dilutions of 1:4 in 1% BSA (Sigma) in 0.05% Tween 20 in PBS in separate dilution plates. The block solution was decanted from plates. 100 μl of diluted test serum was added to each well and incubated at room temperature for 2 h. Serum dilutions were decanted and washed three times. Secondary antibody was diluted (rabbit anti-mouse conjugated with horseradish peroxidase) 1:1000 in 1% BSA in 0.05% Tween 20 in PBS and incubated 1 h at room temperature. Plates were decanted and washed. 100 μl of o-phenylenediamine (OPD) substrate per well was added (0.67 mg/mL) in 0.1M citric acid buffer and incubated 8 min; 100 μl of 1 M $H_2SO_4$ was added to stop the reaction. Absorbance was measured at 490 nm on Spectramax Plus 384 plate reader (Molecular Devices, Sunnyvale, Calif.).

Expression is increased if the SEAP-expressing plasmid injection is administered into the TA (FIG. 5) versus the G muscle, at both 80 and 4 seconds lag time between injection and EP. When the SPc5-12-SEAP plasmid was injected into the TA muscle, serum SEAP levels were 285 fold higher than in control animals that received the plasmid in the absence of EP (P<1.3 E-21); no difference was observed between the 4 and 80 sec lag time for the TA muscle (357±6 vs. 357±6.2 pg/mL/g); the injection under identical conditions into the G muscle resulted in SEAP levels of 90 to 182 fold higher than controls (G 80 sec vs. no EP controls, P<0.003; G 4 sec vs. no EP controls, P<7.7 E-06). When plasmid fragments containing the expression cassettes only were injected in the TA and G (no backbone (NB), but identical promoter, transgene and 3' polyadenylation signal) in an equimolar formulation, the expression levels were 210-250 fold higher than controls that did not receive IM+EP (80 sec vs. no EP, P<1.8 E-08; 4 sec vs. no EP, P<3.8 E-05). SEAP expression in the TA 80 sec was 24% higher than the NB 80 sec group (P<0.008), while TA 4 sec was 37% higher than the NB 4 sec group (P<0.004). Both groups administered $C_{5\text{-}12}$-SEAP and NB without EP (No EP) demonstrated negligible SEAP expression.

Mice—SEAP Expression is Dependent of Formulation

Figure 6:
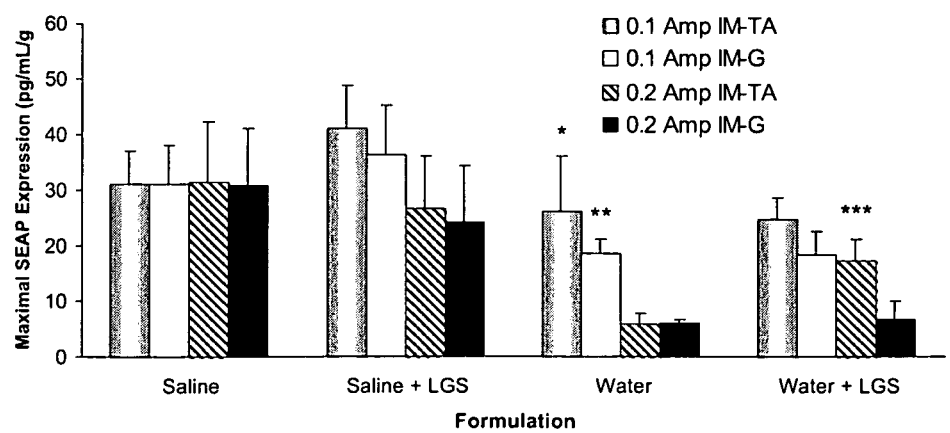
FIG. 6 displays a graph showing SEAP expression driven by the ubiquitous CMV promoter was measured in different muscles in mice under various current settings. The plasmid formulation was tested: saline, saline+LGS, water, or water+ LGS. Saline+LGS formulation at 0.1 A in the TA muscle yielded the highest expression. Animals receiving plasmid formulated into water and electroporation at 0.2 A yielded significantly lower SEAP levels than those receiving 0.1 A for the same muscle (*P<0.05 for TA and P<0.001 For G). When water+LGS was used as the plasmid formulation, the differences in serum SEAP levels were not significant for the TA muscle, but were for the G muscle (*P<0.04).

The differences in SEAP levels when SEAP transgene is under control of a ubiquitous promoter was assessed (versus a muscle-specific promoter as used in the first mice experiment). Expression levels were found to increase if the plasmid injection-EP procedure is performed in the TA (FIG. 6) versus the G muscle (P=0.05). In this particular experiment, saline+LGS formulation resulted in higher serum SEAP levels as compared to saline formulation (41.1±7.9 pg/mL/g vs. 31.0±5.9 pg/mL/g, respectively), although this did not attain statistical significance due to high intra-group variability. Animals that were electroporated at 0.1 A current setting yielded higher SEAP expression than animals that received identical plasmid formulation, delivered at 0.2 A constant current.

Mice—Induction of Anti-SEAP Antibodies

Figure 7:
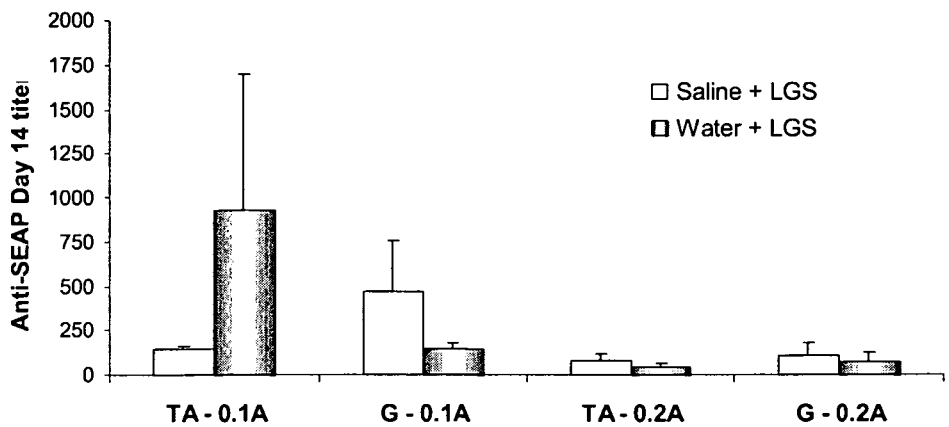
FIG. 7 displays HI titers for anti-SEAP antibodies measured 14 days post-treatment, which were highest in mice treated with 0.1 A of current in the G muscle when plasmid was formulated in (A) saline+LGS and in the TA muscle when formulated in (B) water+LGS.

Formulation of SEAP plasmid with saline+LGS yielded higher protein expression, however, the titers of anti-SEAP antibodies were lower when compared with animals injected with SEAP plasmid formulated in water+LGS (FIG. 7).

Example 4

Antibodies to Influenza in PIGS

Pigs were divided into 10 groups×4 pigs per group for a total of 40 pigs (Table 2). Pigs were acclimated for 4 days, weighed and ear-tagged. On Study Day 0, pigs were weighed, bled and anesthetized using a combination pre-anesthetic for pigs—ketamine—(20 mg/kg), xylazine—(2.2 mg/kg) and atropine (0.04 mg/kg), and then anesthetized using isoflurane (induction at 5%, maintenance at 2-3%). Pigs (n=4/group) were injected with 0.6 mL of CMV-HA (a pVAX based construct that expresses a consensus H5 antigen), CMV-NA (a pVAX based construct that expresses a consensus N1 antigen), and CMV-SEAP (a construct expressing the reporter gene secreted ambryonic alkaline phosphatase, SEAP) plasmid (the last one added to increase plasmid concentration, and viscosity of the solution for the "muscle damage" assessment)+1.0% wt/wt LGS at varying plasmid concentrations and current intensities. The plasmids were prepared according to the materials and methods provided in Example 3, above. After 4 s, animals were electroporated using the adaptive constant current CELLECTRA® intramuscular (IM) system (VGX Pharmaceuticals) equipped with 5 needle electrodes and operated with the following pulse parameters: 52 millisecond pulses, 1 second between pulses, 3 pulses with varying current (0.1, 0.3 and 0.5 A).

TABLE 2

Group for the pig vaccine experiment

| Group | Plasmid | Conc (mg/mL) | Construct (mg)/pig | Total Dose (mg/pig) | Injection Volume | A | n |
|---|---|---|---|---|---|---|---|
| 1 | HA, NA, SEAP | 10 | 2 | 6 | 600 µl | 0.5 | 4 |
| 2 | HA, NA, SEAP | 4 | 0.8 | 2.4 | 600 µl | 0.5 | 4 |
| 3 | HA, NA, SEAP | 1.5 | 0.1 | 0.3 | 600 µl | 0.5 | 4 |
| 4 | HA, NA, SEAP | 10 | 2 | 6 | 600 µl | 0.3 | 4 |
| 5 | HA, NA, SEAP | 4 | 0.8 | 2.4 | 600 µl | 0.3 | 4 |
| 6 | HA, NA, SEAP | 1.5 | 0.1 | 0.3 | 600 µl | 0.3 | 4 |
| 7 | HA, NA, SEAP | 10 | 2 | 6 | 600 µl | 0.1 | 4 |
| 8 | HA, NA, SEAP | 4 | 0.8 | 2.4 | 600 µl | 0.1 | 4 |
| 9 | HA, NA, SEAP | 1.5 | 0.1 | 0.3 | 600 µl | 0.1 | 4 |
| 10 | None | N/A | N/A | N/A | N/A | N/A | 4 |

The area surrounding each injection site was tattooed for rapid identification for biopsy at Days 14 and 35 post-injection.

Pigs were allowed to recover from anesthesia and were closely monitored for 24 hours to ensure full recovery. Any pigs that did not fully recover within 2 to 3 hours post-treatment were noted. Pigs were weighed and bled on Day 10, Day 21 and Day 35. The pigs were administered a second vaccination on Day 21. Blood was collected in separate falcon tubes which were allowed to clot and centrifuged to isolate serum then aliquoted into tubes on ice.

Hemagglutination Inhibition (HI) Assay

Pig sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells as previously described (Stephenson, I., et al., *Virus Res.*, 103(1-2):91-5 (July 2004)).

Figure 8:
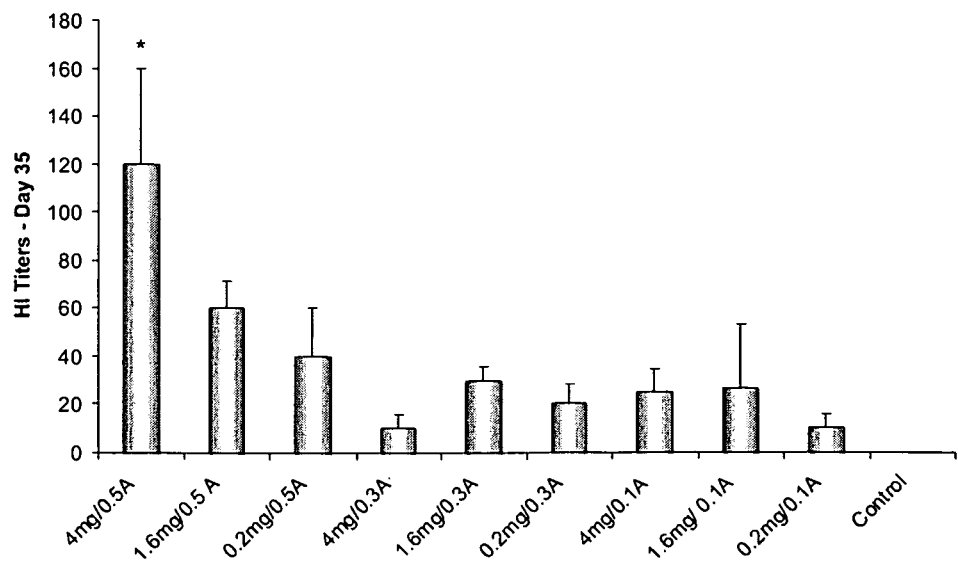
FIG. 8 displays a bar graph of the results of the HI titers in pig serum at Day 35 post-injection. The highest titers were found in the group administered 2 mg of HA-expressing plasmid at a current setting of 0.5 A (120±40; *P=0.11 versus 2 mg/0.3 A and *P=0.02 versus 2 mg/0.1 A). The three groups administered descending doses of plasmid and electroporated at 0.5 A also demonstrated decreasing HI titers.

The highest titers as demonstrated by the HI assay (FIG. 8) were found in sera from the group administered 2 mg of HA-expressing plasmid at a current setting of 0.5 A (120±40; P=0.11 versus 2 mg/0.3 A and P=0.02 versus 2 mg/0.1 A); the titers decreased with the intensity of the electric field for the group that received 2 mg of each plasmid; if either plasmid quantity of current were decreased thereafter, the titers were more variable, and non-different between groups.

The HI titers were highest in the group administered 2 mg of HA-expressing plasmid and electroporated at 0.5 A. Furthermore, the titers decline with descending plasmid doses in the group electroporated at 0.5 A, and with the intensity of the electric field. The lower plasmid quantities or lower current intensities appeared to increase the intra-group variability.

Example 5

Antibodies to Influenza in Ferrets

Twenty male ferrets (Triple F Farms, Sayre, Pa.), 4-6 months of age or at least 1 kg body weight, were used in this study and housed at BIOQUAL, Inc. (Rockville, Md.). The ferret study design is in Table 3. Animals were allowed to acclimate for two weeks prior to the study. Animals were immunized (under anesthesia) at Week 0, 4, and 9. Blood was drawn every 2 weeks.

This study tested the efficacy of HA, NA and M2e-NP DNA vaccine delivered IM followed by electroporation using the CELLECTRA® ® adaptive constant current electroporation intramuscular (IM) system (VGX Pharmaceuticals, The Woodlands, Tex.) in an influenza challenge model in ferrets. The DNA plasmids were prepared according to the materials and methods provided in Example 3, above. As outlined in Table 3, animals in Groups 2, 3 and 4 received 0.2 mg of the respective influenza plasmid vaccine. In order to correct for dose, groups which received 1 plasmid vaccine (Groups 2 and 3) or no vaccine (control Group 1), the difference was made up by pVAX empty vector such that all animals in every group received a total dose of 0.6 mg of plasmid. The conditions of electroporation were, using a 5 needle electrode array: 0.5 Amps, 52 msec pulse width, 1 sec between pulses, 4 sec delay between injection and electroporation.

TABLE 3

Groups for the Influenza challenge experiment in ferrets

| Group | Plasmids/Antigens | Vaccine Dose (mg) per Plasmid | Total vaccine in Total volume | n |
|---|---|---|---|---|
| 1 | None (pVAX only) | 0 mg | 0.6 mg in 0.6 mL | 4 |
| 2 | H5 + pVAX | 0.2 mg | 0.6 mg in 0.6 mL | 4 |
| 3 | NA + pVAX | 0.2 mg | 0.6 mg in 0.6 mL | 4 |
| 4 | H5, NA, M2e-NP | 0.2 mg | 0.6 mg in 0.6 mL | 4 |

Hemagglutination Inhibition (HI) Assay

Figures 9, 10:
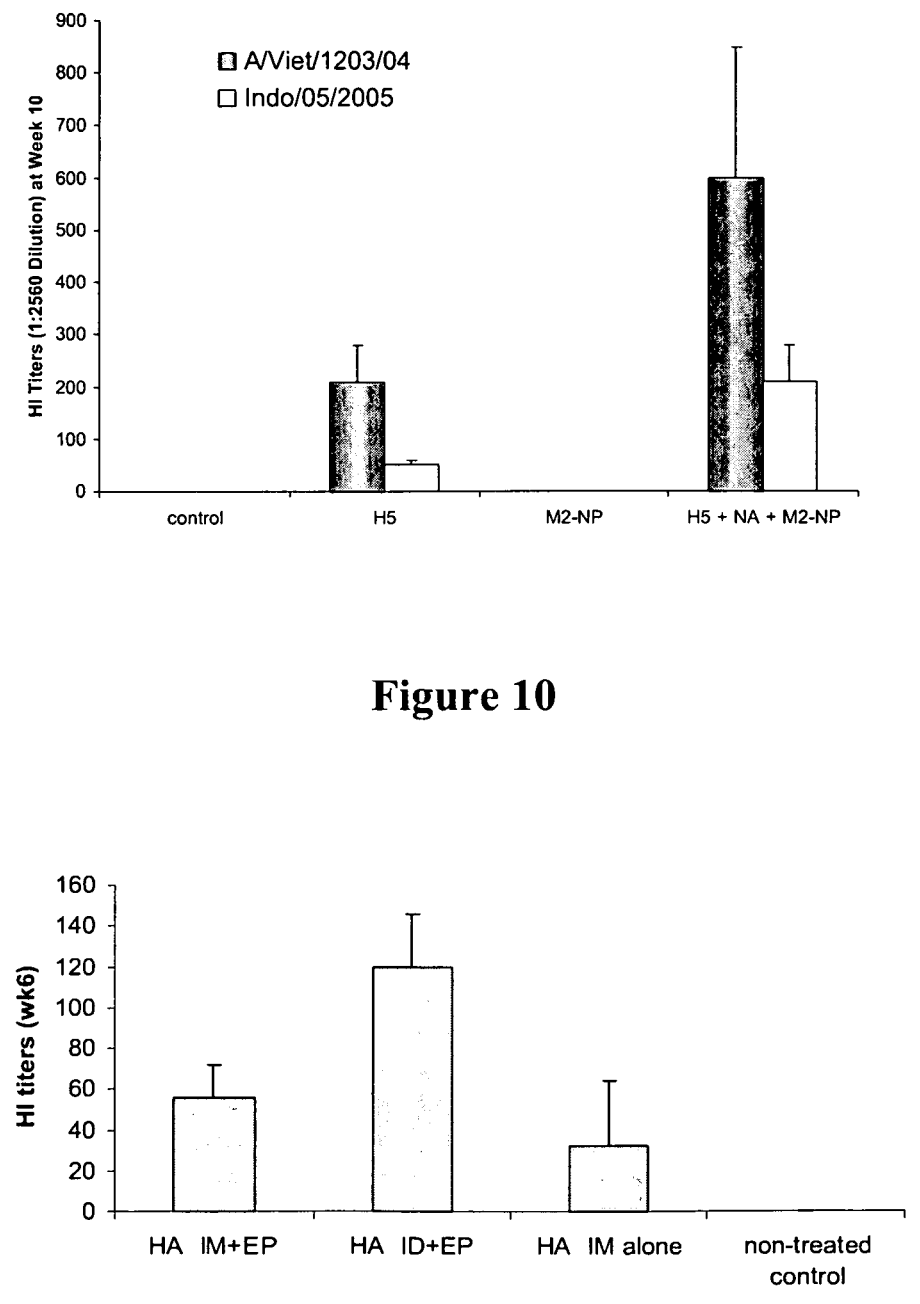

Sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells as previously described (Stephenson, I., et al., *Virus Res.*, 103(1-2):91-5 (July 2004)). The viruses used for the HI assay are reassortant strains we obtained from the Center for Disease Control: A/Viet/1203/2004(H5N1)/PR8-IBCDC-RG (clade 1 virus) and A/Indo/05/2005 (H5N1)/PR8-IBCDC-RG2 (clade 2 virus). The ferret model of influenza infection is considered to be more reflective of human disease and a more rigorous challenge model. Ferrets exhibit similar symptoms to humans infected with influenza and similar tissue tropism with regards to human and avian influenza viruses. Serum collected at different time points throughout the study was used to detect HI activity against $H_5N_1$ viruses. As shown in FIG. 9, both groups containing the consensus H5 specific HA construct attained protective levels of antibody (>1:40) after two immunizations and were also able to inhibit a clade $2H_5N_1$ virus. In other words, the HI assay was positive against both viral strains despite the consensus HA strain was based on clade 1 viruses.

Example 6

Antibodies to Influenza in Primates

Rhesus macaques were immunized in these studies. Animals were acclimated for 2 months prior to the start of experiments. The study progressed as follows: Week 0—performed 1st immunization (plasmid dose administration) and baseline bleed; Week 2 performed bleed; Week 3 performed 2nd immunization (plasmid dose administration); Week 5 performed bleed; Week 6 performed 3rd immunization (plasmid dose administration) and bleed; Week 8 performed bleed.

TABLE 4

| Study Group | DNA Constructs | Nr. | Route of Admin | Dose | Total DNA (mg) |
|---|---|---|---|---|---|
| A | DNA 6 + 9 | 5 | IM CELLECTRA ® EP | 1 mg/Const | 2 |
| B | DNA 6 + 9 | 5 | ID CELLECTRA ® EP | 1 mg/Const | 2 |
| C | DNA 1 + 6 + 9 + 10 | 5 | IM Syringe | 1 mg/Const | 4 |
| D | Negative Control | 5 | N/A | | 0 |

| DNA Construct # | Encoding Antigen |
|---|---|
| 1 | Non-influenza antigen control plasmid |
| 6 | Influenza H5 consensus |
| 9 | Non-influenza antigen control plasmid |
| 10 | Non-influenza antigen control plasmid |

All plasmids were formulated at 10 mg/mL in water for injection+1% LGS, as described in previous examples, above, and mixed into a single solution PER STUDY GROUP (S) (Groups C, D, G, and H, in above table, Table 4). The correct injection volume for each group designated IM CELLECTRA® EP (VGX Pharmaceuticals), ID CELLECTRA® EP (VGX Pharmaceuticals), and 1M Syringe was calculated. For the ID administration, if the required injection volume surpassed 100 μL per site, the formulation was split into a number of injection sites (2, 3, or 6 depending on how many total mg of vaccine were administered). The animals that received IM injection(s) were given the entire formulation in one single site.

The CELLECTRA® adaptive constant current device used in the pigs experiments, ferret experiments and nonhuman experiments described in the Examples. The electroporation conditions were as following: for the IM injection and electroporation groups the conditions were: 0.5 Amps, 52 msec/pulse, three pulses, 4 sec delay between plasmid injection and electroporation. For the ID injection and electroporation groups the conditions were: 0.2 Amps, 52 msec/pulse, three pulses, 4 sec delay between plasmid injection and electroporation.

Hemagglutination Inhibition (HI) Assay—monkey sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of 1/10. HI assays were performed in V-bottom 96-well microtiter plates, using four HA units of virus and 1% horse red blood cells. The data presented herein are the results after the second immunization (bleed collected before the third immunization).

HI titers were measured three weeks after the second immunization. The results can be seen displayed in the graph in FIG. 10. Monkeys receiving the HA plasmid vaccine via ID injection followed by electroporation demonstrated more than twice the average titers of the IM+EP group and almost three times the average titers of the IM group alone (*P<0.03). Non-treated controls did not exhibit any HI titrs.

What is claimed:

1. A method of generating antibodies in a mammal against recombinant antigens, wherein said antigen is influenza HA, influenza NA, or influenza M2e-NP, using DNA plasmids capable of expressing said antigens in cells of said mammal, comprising:
   injecting into tissue of said mammal a DNA plasmid consisting essentially of an encoding sequence operably linked to a promoter, wherein the encoding sequence encodes a protein consisting of the antigen,
   electroporating said tissue with an electroporation device capable of delivering an electrical pulse effective to electroporate cells of said tissue to allow entry of said DNA plasmid and expression of said antigen, and
   allowing said mammal to respond to said expressed antigen in order to generate antibodies to said antigen
   wherein the electroporating step comprises delivering a current of 0.5 Amp.

2. The method of claim 1, wherein said antibodies are neutralizing antibodies.

3. The method of claim 1, wherein said antibodies are isotypes IgG1 or IgG2a.

4. The method of claim 1, said electroporating step comprising electroporating said tissue with a constant-current electroporation device.

5. The method of claim 1, wherein said current is a constant current throughout pulse duration.

6. The method of claim 1, wherein said electroporating step is undertaken from about 1 sec to about 20 sec after said injecting step.

7. The method of claim 1, wherein said electorporating step is undertaken from about 1 sec to about 10 sec after said injecting step.

8. The method of claim 1, wherein said electorporating step is undertaken from about 1 sec to about 5 sec after said injecting step.

9. The method of claim 1, wherein said electorporating step is undertaken about 4 sec after said injecting step.

10. The method of claim 1, said electroporating step comprising delivering more than one electrical pulse.

11. The method of claim 1, said electroporating step comprising delivering three electrical pulses.

12. The method of claim 10, said electroporating step comprising pausing about 0.1 sec to about 5 sec between electrical pulses.

13. The method of claim 10, said electroporating step comprising pausing about 1 sec between electrical pulses.

14. The method of claim 1, wherein said DNA plasmid is injected in said injecting step in concentrations of greater than 1 mg/ml.

15. The method of claim 14, wherein said concentrations of DNA plasmid is greater than 2 mg/ml.

16. The method of claim 14, wherein said concentrations of DNA plasmid is greater than 4 mg/ml.

17. The method of claim 1, wherein said method is repeated in a subsequent day.

18. The method of claim 1, further comprising delivering a protein boost of said antigen to said mammal at a subsequent day.

19. The method of claim 1, wherein the injecting step is injecting into intramuscular or intradermic tissue see claim 40.

20. The method of claim 1, wherein the injecting step further comprises injecting an adjuvant.

21. A method of isolating antibodies specific against desired antigens, wherein said antigen is influenza HA, influenza NA, or influenza M2e-NP and wherein said antibodies are generated in a mammal using DNA plasmids capable of expressing said antigens in cells of said mammal, comprising:
   injecting into tissue of said mammal a DNA plasmid consisting essentially of an encoding sequence operably linked to a promoter, wherein the encoding sequence encodes a protein consisting of the antigen,
   electroporating said tissue with an electroporation device capable of delivering an electrical pulse effective to electroporate cells of said tissue to allow entry of said DNA plasmid and expression of said antigen,
   allowing said mammal to respond to said expressed antigen in order to generate antibodies to said antigen,
   collecting serum from said mammal, and
   extracting the antibodies from the serum
   wherein the electroporating step comprises delivering a current of 0.5 Amp.

22. The method of claim 21, further comprising purifying the extracted antibodies.

23. The method of claim 21, wherein said antibodies are neutralizing antibodies.

24. The method of claim 21, wherein said antibodies are isotypes IgG1 or IgG2a.

25. The method of claim 21, said electroporating step comprising electroporating said tissue with a constant-current electroporation device.

26. The method of claim 21, wherein said current is a constant current throughout pulse duration.

27. The method of claim 21, wherein said electroporating step is undertaken from about 1 sec to about 20 sec after said injecting step.

28. The method of claim 21, wherein said electroporating step is undertaken from about 1 sec to about 10 sec after said injecting step.

29. The method of claim 21, wherein said electroporating step is undertaken from about 1 sec to about 5 sec after said injecting step.

30. The method of claim 21, wherein said electroporating step is undertaken about 4 sec after said injecting step.

31. The method of claim 21, said electroporating step comprising delivering more than one electrical pulse.

32. The method of claim 21, said electroporating step comprising delivering three electrical pulses.

33. The method of claim 30, said electroporating step comprising pausing about 0.1 sec to about 5 sec between electrical pulses.

34. The method of claim 30, said electroporating step comprising pausing about 1 sec between electrical pulses.

35. The method of claim 21, wherein said DNA plasmid is injected in said injecting step in concentrations of greater than 1 mg/ml.

36. The method of claim 35, wherein said concentrations of DNA plasmid is greater than 2 mg/ml.

37. The method of claim 35, wherein said concentrations of DNA plasmid is greater than 4 mg/ml.

38. The method of claim 21, wherein said method is repeated in a subsequent day.

39. The method of claim 21, further comprising delivering a protein boost of said antigen to said mammal at a subsequent day.

40. The method of claim 21, wherein the injecting step is either injecting into intramuscular or intradermic tissue.

41. The method of claim 21, wherein the injecting step further comprises injecting an adjuvant.

* * * * *